(12) United States Patent
Uzawa et al.

(10) Patent No.: US 12,092,637 B2
(45) Date of Patent: Sep. 17, 2024

(54) METHOD FOR MEASURING FIBROBLAST GROWTH FACTOR-23 AND REAGENT THEREFOR

(71) Applicant: Hitachi Chemical Diagnostics Systems Co., Ltd., Tokyo (JP)

(72) Inventors: Koji Uzawa, Shizuoka (JP); Emiko Suzuki, Shizuoka (JP); Kazuyuki Ikeda, Tokyo (JP); Kazuki Morita, Shizuoka (JP)

(73) Assignee: HITACHI CHEMICAL DIAGNOSTICS SYSTEMS CO., LTD., Tokyo (JP)

( * ) Notice: Subject to any disclaimer, the term of this patent is extended or adjusted under 35 U.S.C. 154(b) by 958 days.

(21) Appl. No.: 16/549,387

(22) Filed: Aug. 23, 2019

(65) Prior Publication Data

US 2019/0376961 A1 Dec. 12, 2019

Related U.S. Application Data

(63) Continuation of application No. 13/819,398, filed as application No. PCT/JP2011/069734 on Aug. 31, 2011, now Pat. No. 10,422,796.

(30) Foreign Application Priority Data

Aug. 31, 2010 (JP) ................. 2010-193213

(51) Int. Cl.
*G01N 33/543* (2006.01)
*G01N 33/538* (2006.01)
*G01N 33/74* (2006.01)

(52) U.S. Cl.
CPC ..... *G01N 33/54333* (2013.01); *G01N 33/538* (2013.01); *G01N 33/54326* (2013.01); *G01N 33/74* (2013.01); *G01N 2333/50* (2013.01)

(58) Field of Classification Search
CPC .............................. G01N 33/54333
See application file for complete search history.

(56) References Cited

U.S. PATENT DOCUMENTS

| 4,628,037 | A | 12/1986 | Chagnon et al. |
| 5,817,469 | A | 10/1998 | Hubner-Parajsz et al. |
| 7,439,026 | B2 | 10/2008 | Pandian et al. |
| 10,422,796 | B2 * | 9/2019 | Uzawa ............ G01N 33/74 |
| 2003/0198998 | A1 | 10/2003 | Uttenthal |
| 2005/0003493 | A1 | 1/2005 | Hutchinson |
| 2005/0048058 | A1 | 3/2005 | Yamazaki et al. |
| 2005/0106755 | A1 | 5/2005 | Zahradnik et al. |
| 2006/0064249 | A1 | 3/2006 | Clark et al. |
| 2010/0112727 | A1 | 5/2010 | Todd et al. |

FOREIGN PATENT DOCUMENTS

| CN | 1639193 A | 7/2005 |
| CN | 1667413 A | 9/2005 |
| CN | 1928560 A | 3/2007 |
| JP | H08-501390 A | 2/1996 |
| JP | 2004-504063 A | 2/2004 |
| JP | 2005-062087 A | 3/2005 |
| JP | 2007-178356 A | 7/2007 |
| JP | 2008-017790 A | 1/2008 |
| KR | 10-2004-0073518 A | 8/2004 |
| WO | 94/07139 A1 | 3/1994 |
| WO | 02/08271 A1 | 1/2002 |
| WO | 03/057733 A1 | 7/2003 |
| WO | 2010/039179 A1 | 4/2010 |

OTHER PUBLICATIONS

Sokoll et al., "Rapid Intraoperative Immunoassay of Parathyroid Hormone and Other Hormones: A new Paradigm for Point-of-Care Testing," Clinical Chemistry, 50 (7): 1126-1135 (2004).
Boudou et al., "Third- or Second-Generation Parathyroid Hormone Assays: A Remaining Debate in the Diagnosis of Primary Hyperparathyroidism," The Journal of Clinical Endocrinology & Metabolism, 90 (12): 6370-6372 (2005).

(Continued)

*Primary Examiner* — Albert M Navarro
(74) *Attorney, Agent, or Firm* — Morgan, Lewis & Bockius LLP

(57) ABSTRACT

A method for measuring fibroblast growth factor-23 (FGF-23) in a sample, which comprise the following steps:
(1) reacting, in an aqueous medium, FGF-23 in a sample with magnetic particles, a first antibody or a fragment thereof which binds to FGF-23, and a second antibody or a fragment thereof which binds to FGF-23, to form on the magnetic particles an immunocomplex comprising the first antibody or a fragment thereof which binds to FGF-23, FGF-23, and the second antibody or a fragment thereof which binds to FGF-23;
(2) collecting the magnetic particles in the reaction mixture after step (1) by magnetic force, and separating the magnetic particles collected by magnetic force from the other components; and
(3) measuring the immunocomplex on the magnetic particles separated in step (2).

The present invention provides a method for measuring FGF-23 in a sample, which have a high sensitivity and have a wide measurement range.

7 Claims, 6 Drawing Sheets

(56) References Cited

OTHER PUBLICATIONS

Cantor et al., "Lack of Comparability of Intact Parathyroid Hormone measurements Among Commercial Assays for End-Stage Renal Disease Patients: Implication for Treatment Decisions," Clinical Chemistry, 52 (9): 1771-1776 (2006).

Cantor, "Parathyroid Hormone Assay Drift: An Unappreciated Problem in Dialysis Patient Management," Seminars in Dialysis, 18 (5): 359-364 (2005).

"Quiet Diagnostics to Pay U.S. $302 Million to Resolve Allegations That a Subsidiary Sold Misbranded Test Kits," Department of Justice, Justice News, Apr. 15, 2009.

Butch, "Dilution Protocols for Detection of Hook Effects/Prozone Phenomenon," Letter to the Editor, Clinical Chemistry, 46 (10): 1719-1720 (2000).

Kazama et al., "Pretreatment serum FGF-23 levels predict the efficacy of calcitriol therapy in dialysis patients," Kidney International, 67: 1120-1125 (2005).

Nakanishi et al., "Serum fibroblast growth factor-23 levels predict the future refractory hyperparathyroidism in dialysis patients," Kidney International, 67: 1171-1178 (2005).

Extended European Search Report issued in European Patent Application No. 16176905.4 dated Sep. 21, 2016.

Chinese Search Report issued in Chinese Patent Application No. 2011800518195 dated Jun. 24, 2014.

Extended European Search Report issued in European Patent Application No. 11821852.8 dated Feb. 18, 2014.

Jonsson et al., "Fibroblast Growth Factor 23 in Oncogenic Oteomalacia and X-Linked Hypophosphatemia," The New England Journal of Medicine, 348 (17): 1656-1663 (2003).

Yamashita, "Discovery of a Novel Hormone Controlling Renal Phosphorus Transport," Kidney Metab Bone Dis, 15 (4): 351-356 (2002).

International Search Report issued in International Patent Application No. PCT/JP2011/069734 dated Nov. 8, 2011.

U.S. Appl. No. 14/113,805, filed Feb. 13, 2014.

* cited by examiner

METHOD FOR MEASURING FIBROBLAST GROWTH FACTOR-23 AND REAGENT THEREFOR

TECHNICAL FIELD

The present invention relates to a method for measuring fibroblast growth factor-23 (hereinafter indicated as FGF-23) in a sample, and a reagent for measuring FGF-23.

BACKGROUND ART

FGF-23 is a member of the fibroblast growth factor (FGF) family and a polypeptide containing of 251 amino acids, which is produced mainly in bone tissues and acts on the kidney to inhibit reabsorption of phosphorus in the renal tubules. In recent years, FGF-23 has been suggested to be involved in diseases such as hypophosphatemic rickets, tumor-induced osteomalacia, and renal failure (see Non-Patent Document 1).

FGF-23 is formed by dissociation of the 24 amino acids at the N-terminus to give a polypeptide containing 227 amino acids, and modified to add sugar chains, and released to the outside of cells as an approximately 32.5-kDa mature protein. Moreover, the bond between position 197 and position 198 from the N-terminus of FGF-23 is cleaved by thrombin, and the fragment of position 198 to position 251 exists in the blood as a C-terminal fragment.

To date, antibodies against FGF-23 have been obtained (see Patent Documents 1 and 2; and Non-Patent Document 2), immunoassays for FGF-23 in the serum or plasma which use these antibodies have been reported (see Patent Document 1 and Non-Patent Document 2), and measurement kits based on these measurement methods are also commercially available [Human Intact FGF-23 ELISA Kit (Immutopies), Human FGF-23 (C-Term) ELISA Kit (Immutopics), and FGF-23 measurement reagent (Kainos)].

However, immunoassays to date are measuring methods using plates, and these methods have the problems of having low measurement sensitivity and a narrow measurement range.

Particularly in chronic kidney disease (CKD) patients and dialysis patients, the specimens are in the concentration range of several pg/mL to several tens of thousands of pg/mL, and there were problems such as, in low concentration samples, correct measurement values could not be obtained due to poor accuracy and, in high concentration specimens, the measurement range was surpassed.

PRIOR ART DOCUMENTS

Patent Documents

[Patent Document 1] WO 2003/057733 pamphlet
[Patent Document 2] Japanese Patent Kohyvo Publication No. (JP-A) 2004-504063 (unexamined, Japanese national phase publication corresponding to a non-Japanese international application)

Non-Patent Documents

[Non-Patent Document 1] Jin to Kotsu Taisha (Kidney and Metabolic Bone Diseases), vol. 15. No. 4, p. 351-356 (2002).
[Non-Patent Document 2] N ENGL J MED, vol. 348, No. 17, p. 1656-1663 (2003).

SUMMARY OF THE INVENTION

Problems to be Solved by the Invention

An objective of the present invention is to provide a method and a reagent for measuring FGF-23 in a sample, which have a high sensitivity and a wide measurement range.

Means for Solving the Problems

The present inventors carried out dedicated research to solve the above-mentioned problems and, as a result, found that an immunoassay which uses magnetic particles as a carrier enables measurement of FGF-23 with a high sensitivity and wide measurement range, and completed the present invention. More specifically, the present invention relates to [1] to [10] below:

[1] a method for measuring FGF-23 in a sample, wherein the method comprises the steps of:
   (1) reacting, in an aqueous medium, FGF-23 in a sample with a magnetic particle, a first antibody or a fragment thereof which binds to FGF-23, and a second antibody or a fragment thereof which binds to FGF-23, to form on the magnetic particle an immunocomplex comprising the first antibody or a fragment thereof which binds to FGF-23, FGF-23, and the second antibody or a fragment thereof which binds to FGF-23;
   (2) collecting the magnetic particle in the reaction mixture after step (1) by magnetic force, and separating the magnetic particle collected by magnetic force from the other components; and
   (3) measuring the immunocomplex on the magnetic particle separated in step (2);
[2] the method of [1], wherein the second antibody is a labeled antibody;
[3] the method of [2], wherein the labeled antibody is an alkaline phosphatase-labeled antibody;
[4] the method of any one of [1] to [3], wherein measurement of the immunocomplex on the magnetic particle in step (3) is carried out by measurement of chemiluminescence;
[5] the method of any one of [1] to [4], wherein the sample is serum or plasma;
[6] a reagent for measuring FGF-23 in a sample, which comprises a magnetic particle, a first antibody or a fragment thereof which binds to FGF-23, and a second antibody or a fragment thereof which binds to FGF-23;
[7] the reagent of [6], wherein the second antibody is a labeled antibody;
[8] the reagent of [7], wherein the labeled antibody is an alkaline phosphatase-labeled antibody;
[9] the reagent of any one of [6] to [8], which further comprises a reagent for measuring chemiluminescence; and
[10] the reagent of any one of [6] to [9], wherein the sample is serum or plasma.

Effects of the Invention

The present invention provides a method and a reagent for measuring FGF-23 in a sample, which have a high sensitivity and have a wide measurement range.

Figure 1:
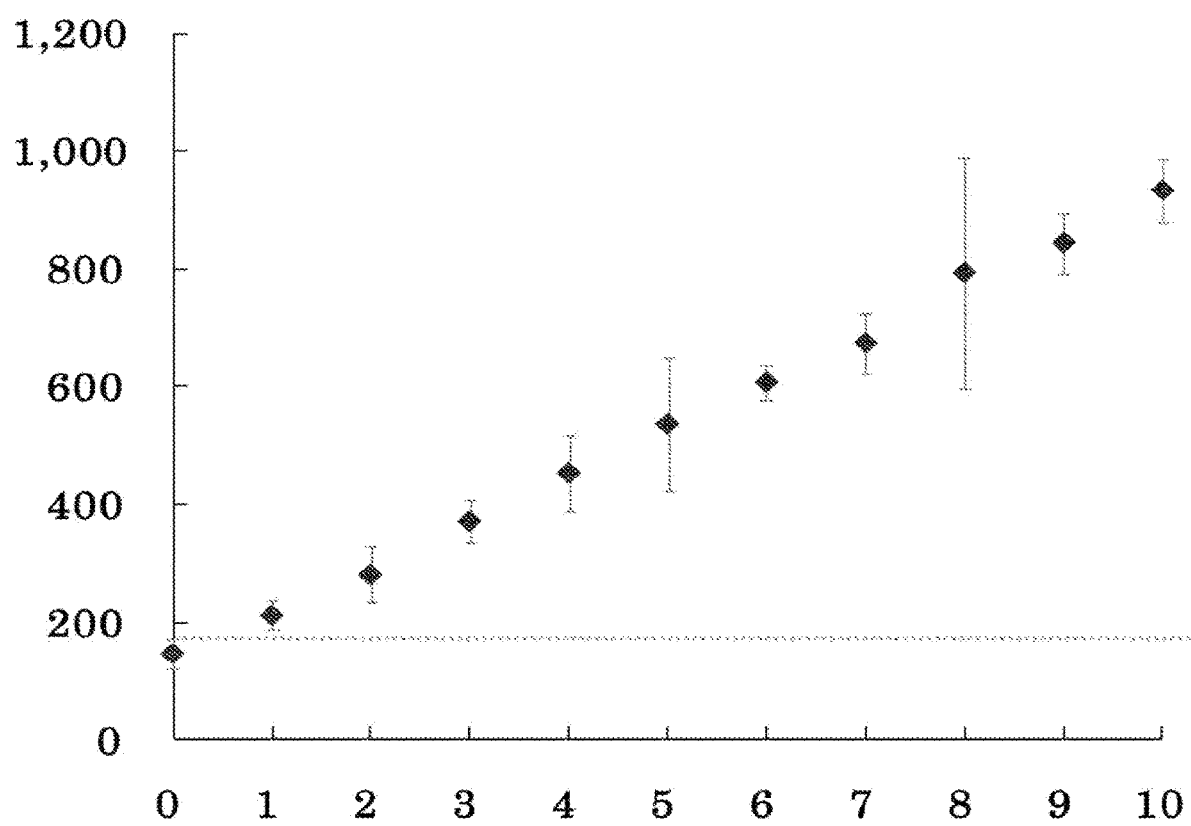
FIG. 1 shows a graph indicating the minimum measurable concentration using the method for measuring FGF-23 of Example 1, and shows the relationships between the FGF-23 concentrations in the samples and the luminescence levels. The horizontal axis shows the FGF-23 concentration (pg/mL), and the vertical axis shows the luminescence level (RLU). The mark "I" indicates the ranges of the averages value±2SD. Furthermore, the dotted line indicates the luminescence level of blank+2SD.

MODE FOR CARRYING OUT THE INVENTION (Measurement Methods)

The method for measuring FGF-23 in a sample according to the present invention is an immunoassay method for FGF-23 in a sample based on the Sandwich method, which uses magnetic particles as a carrier and comprises the following steps:
(1) reacting in an aqueous medium, FGF-23 in a sample with magnetic particles, a first antibody or a fragment thereof which binds to FGF-23, and a second antibody or a fragment thereof which binds to FGF-23, to form on the magnetic particles immunocomplexes comprising the first antibody or a fragment thereof which binds to FGF-23, FGF-23, and the second antibody or a fragment thereof which binds to FGF-23;
(2) collecting the magnetic particles in the reaction mixture after step (1) using magnetic force, and separating the magnetic particles collected by magnetic force from the other components; and
(3) measuring the immunocomplexes on the magnetic particles separated in step (2).

<Step (1)>

In step (1), FGF-23 in the sample reacts in an aqueous medium with the magnetic particles, the first antibody or a fragment thereof which binds to FGF-23, and the second antibody or a fragment thereof which binds to FGF-23 to form on the magnetic particles an immunocomplex comprising the first antibody or a fragment thereof which binds to FGF-23, FGF-23, and the second antibody or a fragment thereof which binds to FGF-23.

Herein, the reaction of FGF-23 in the sample with the magnetic particles, the first antibody or a fragment thereof which binds to FGF-23, and the second antibody or a fragment thereof which binds to FGF-23 can be any reaction as long as it forms, on the magnetic particles, an immunocomplex comprising the first antibody or a fragment thereof which binds to FGF-23, FGF-23, and the second antibody or a fragment thereof which binds to FGF-23. For example, FGF-23 in the sample can be reacted with the magnetic particles and the first antibody or a fragment thereof which binds to FGF-23 to form on the magnetic particles an immunocomplex of the first antibody or a fragment thereof which binds to FGF-23 and FGF-23, then this can be reacted with a second antibody or a fragment thereof which binds to FGF-23; or alternatively, FGF-23 in the sample can be simultaneously reacted with the magnetic particles, the first antibody or a fragment thereof which binds to FGF-23, and the second antibody or a fragment thereof which binds to FGF-23. In case formation of an immunocomplex of the first antibody or a fragment thereof which binds to FGF-23 and FGF-23 on the magnetic particles is followed by reaction of the immunocomplex with the second antibody or a fragment thereof which binds to FGF-23, a washing step can be set up after formation of the immunocomplex.

In step (1), the first antibody or a fragment thereof which binds to FGF-23 and the magnetic particles can be preliminary bonded prior to reaction with FGF-23 in the sample. Examples of bonding of the first antibody or a fragment thereof which binds to FGF-23 to the magnetic particles include bonding by physical adsorption, bonding via a linker, and bonding which uses the interaction between two substances having affinity to each other such as antibody Fc region/Fc region-binding antibody and avidins (avidin, streptavidin, NeutrAvidin, etc.)/biotin. In case of using the interaction between the antibody Fc region and the Fc region-binding antibody, for example, the first antibody or a fragment thereof can be bonded onto the magnetic particles through the interaction between the Fc region-binding antibody fixed onto the magnetic particles and the first antibody or a fragment thereof. In case of using the interaction between avidins and biotin, for example, the first antibody or a fragment thereof can be bonded onto the magnetic particles through the interaction between the avidin fixed onto the magnetic particles and the biotin in the biotinylated first antibody or a fragment thereof.

The concentration of magnetic particles in the reaction solution is not particularly limited as long as it is a concentration that enables measurement of FGF-23 of the present invention, and is ordinarily 0.1 mg/mL to 10 mg/mL. The reaction temperature is not particularly limited as long as it is a temperature that enables measurement of FGF-23 of the present invention, and is ordinarily 0° C. to 50° C., preferably 4° C. to 45° C., and particularly preferably 20° C. to 40° C. The reaction time is not particularly limited as long as it is a time that enables measurement of FGF-23 of the present invention, and is ordinarily 5 minutes to 1 hour, and preferably 5 minutes to 20 minutes.

In case of using magnetic particles to which the first antibody or a fragment thereof which binds to FGF-23 has been immobilized in advance, the magnetic particles to which the first antibody or a fragment thereof which binds to FGF-23 has been bonded can be produced by any method as long as the method for measuring FGF-23 of the present invention is enabled. For example, by adding a solution of 0.1 µg/mL to 10 pg/mL of the first antibody or a fragment thereof to a suspension solution of 0.1 mg/mL to 10 mg/mL of the magnetic particles and carrying out the reaction for 5 minutes to one hour at 37° C., magnetic particles to which the first antibody or a fragment thereof is bound can be produced.

Furthermore, in case the formation of an immunocomplex comprising the FGF-23 in the sample, the first antibody or a fragment thereof which binds to FGF-23, and the magnetic particles is followed by the binding of the second antibody or a fragment thereof which binds to FGF-23 to the immunocomplex in step (1), a step of washing the immunocomplex-bound magnetic particles can be set up before the binding of the second antibody. Washing of the magnetic particles can be any washing, as long as it allows formation on the magnetic particles of immunocomplexes comprising the first antibody or a fragment thereof which binds to FGF-23, FGF-23, and the second antibody or a fragment thereof which binds to FGF-23. Examples include methods of washing the magnetic particles by removing components other than the magnetic particles from the reaction mixture after the reaction that forms on the magnetic particles the immunocomplexes of FGF-23 and the first antibody or a fragment thereof which binds to FGF-23, and adding a washing solution to the reaction vessel containing the remaining magnetic particles; and methods of washing the magnetic particles by adding the washing solution to the reaction mixture after the reaction and, at the same time, removing the components other than the magnetic particles. Removal of components other than the magnetic particles can be carried out, for example, by collecting the magnetic particles by magnetic force and aspirating the remaining components. The washing solution is not particularly limited as long as the washing solution enables measurement of the FGF-23 of the present invention, and examples include the aqueous medium mentioned below and aqueous media produced by adding a surfactant to the aqueous medium mentioned below. Examples of the surfactants include non-ionic surfactants such as Tween 20.

Further, a salt can also be present in step (1). The salt is not particularly limited as long as the salt enables the method for measuring FGF-23 of the present invention. Examples include lithium chloride, sodium chloride, potassium chloride, calcium chloride, magnesium chloride, ammonium chloride, lithium bromide, sodium bromide, potassium bromide, calcium bromide, magnesium bromide, and ammonium bromide; and sodium chloride is preferred. The concentration of the salt in the reaction is not particularly limited as long as the concentration enables the measurement method of the present invention, and is for example, 40 mmol/L to 400 mmol/L and preferably 70 mmol/L to 250 mmol/L.

Furthermore, in step (1), a metal ion, a sugar, an antiseptic agent, a protein, a surfactant, a protein stabilizer, and such can also be present. Examples of the metal ion include magnesium ion, manganese ion, and zinc ion. Examples of the sugar include mannitol and sorbitol. Examples of the antiseptic agent include sodium azide, antibiotics (streptomycin, penicillin, gentamicin, etc.), BioAce, and ProClin 300. Examples of the protein include bovine serum albumin (BSA), fetal bovine serum (FBS), casein, and BlockAce (manufactured by Dainippon Pharmaceutical Co., Ltd.). Examples of the surfactant include cationic surfactants, anionic surfactants, amphoteric surfactants, and nonionic surfactants. Examples of the protein stabilizer include peroxidase stabilizing buffer and alkaline phosphatase stabilizing buffer.

<Step (2)>

In step (2), the magnetic particles after step (1), or specifically, the magnetic particles to which immunocomplexes comprising the first antibody or a fragment thereof which binds to FGF-23, FGF-23, and the second antibody or a fragment thereof which binds to FGF-23 are bound, are collected by magnetic force, and the magnetic particles collected by magnetic force are separated from the other components. The magnetic force for collecting the magnetic particles is not particularly limited as long as it is a magnetic force that enables the measurement of FGF-23 of the present invention. The separation of the magnetic particles collected by magnetic force from the other components is not particularly limited as long as it is a separation that enables the measurement of FGF-23 of the present invention.

After step (2), or simultaneously with step (2), a step of washing the magnetic particles to which immunocomplexes comprising the first antibody or a fragment thereof which binds to FGF-23, FGF-23, and the second antibody or a fragment thereof which binds to FGF-23 are bound can be included. The magnetic particles can be washed, for example, by an aforementioned method.

<Step (3)>

Next, in step (3), the immunocomplexes on the magnetic particles separated in step (2) can be measured to measure the FGF-23 in the sample. Examples of the method for measuring the immunocomplexes include the following methods:

(1) In case the second antibody or a fragment thereof which binds to FGF-23 is not labeled The immunocomplexes on the separated magnetic particles can be measured by reacting a labeled third antibody or a fragment thereof, in which a label is bound to a third antibody or a fragment thereof that binds to the second antibody or a fragment thereof, with the magnetic particles to which the immunocomplexes comprising the first antibody or a fragment thereof, FGF-23, and the second antibody or a fragment thereof are bound to form, on the magnetic particles, immunocomplexes comprising the first antibody or a fragment thereof, FGF-23, the second antibody or a fragment thereof, and the third antibody or a fragment thereof, and then measuring the label in these immunocomplexes. Examples of the third antibody or a fragment thereof that binds to the second antibody or a fragment thereof include antibodies or a fragment thereof that bind to the Fe region of the second antibody. Measurement of the label is not particularly limited as long as it is a method that enables measurement of an immunocomplex on the separated magnetic particles. Examples include measurement of chemiluminescence, measurement of fluorescence, and measurement of absorbance; and measurement of chemiluminescence is preferred.

(2) In case the second antibody or a fragment thereof which binds to FGF-23 is labeled The immunocomplexes on the separated magnetic particles can be measured by measuring the label in the immunocomplexes comprising the first antibody or a fragment thereof, FGF-23, and the labeled second antibody or a fragment thereof which binds to FGF-23, which are formed on the magnetic particles. Measurement of the label is not particularly limited as long as it is a method that enables measurement of an immunocomplex on the separated magnetic particles. Examples include measurement of chemiluminescence, measurement of fluorescence, and measurement of absorbance; and measurement of chemiluminescence is preferred.

(A) Measurement of Chemiluminescence

Measurement of chemiluminescence can be carried out by methods such as the following.

(A-1) In Case the Label is an Enzyme

In case the label is an enzyme, for example, the measurement can be carried out by allowing a substrate that produces light upon reacting with that enzyme to act on the labeled antibody or a fragment thereof, and measuring the intensity of the produced light (hv) using a luminescence intensity meter or such. The enzyme is not particularly limited as long as it can react with a substrate of the enzyme and produce light, and examples include alkaline phosphatase, peroxidase, β-D-galactosidase, and luciferase.

In case of using alkaline phosphatase as the enzyme, examples of the substrate of alkaline phosphatase which reacts with alkaline phosphatase to produce light include 3-(2'-spiroadamantane)-4-methoxy-4-(3'-phosphoryloxy) phenyl-1,2-dioxetane disodium salt (AMPPD), 2-chloro-5-{4-methoxyspiro[1,2-dioxetane-3,2'-(5'-chloro)tricyclo [3.3.1.13,7]decane]-4-yl}phenyl phosphate disodium salt (CDP-Star™), 3-{4-methoxyspiro[1,2-dioxetane-3,2'-(5'-chloro)tricyclo[3.3.1.13,7]decane]-4-yl}phenylphosphate disodium salt (CSPD™), [10-methyl-9(10H)-acridinylidene]phenoxymethylphosphate disodium salt (Lumigen™ APS-5), and 9-(4-chlorophenylthiophosphoryloxymethylidene)-10-methylacridone disodium salt.

In case of using peroxidase as the enzyme, examples of the substrate of peroxidase which reacts with peroxidase to produce light include a combination of hydrogen peroxide and a luminescent compound. Examples of the luminescent compound include the luminol compound and the lucigenin compound.

In case of using β-D-galactosidase as the enzyme, examples of the substrate of β-D-galactosidase which reacts with β-D-galactosidase to produce light include Galacton-Plus (manufactured by Applied Biosystems).

In case of using luciferase as the enzyme, examples of the substrate of luciferase which reacts with luciferase to produce light include luciferin and coelenterazine.

(A-2) In Case the Label is a Luminescent Substance

In case the label is a luminescent substance, for example, the measurement can be carried out by measuring the intensity of light originated from the luminescent substance in the formed immunocomplexes using a luminescence intensity meter or the like. The luminescent substance is not particularly limited as long as it is a luminescent substance that enables the measurement of the present invention, and examples include acridinium and derivatives thereof, ruthenium complex compounds, and lophine.

(B) Measurement of Fluorescence

Fluorescence can be measured by methods such as the following.

(B-1) in Case the Label is an Enzyme

In case the label is an enzyme, for example, the measurement can be carried out by allowing a substrate that produces fluorescence upon reacting with that enzyme to act on the labeled antibody or a fragment thereof, and measuring the intensity of the produced fluorescence on a fluorescence intensity meter or such. The enzyme is not particularly limited as long as it can react with a substrate of the enzyme to produce fluorescence, and examples include peroxidase, β-D-galactosidase, and β-glucuronidase.

In case of using peroxidase as the enzyme, examples of the substrate of peroxidase which reacts with peroxidase to produce fluorescence include a combination of hydrogen peroxide and a fluorescent compound. Examples of the fluorescent compound include 4-hydroxyphenylacetic acid, 3-(4-hydroxyphenyl)propionic acid, and coumarin.

In case of using β-D-galactosidase as the enzyme, examples of the substrate of β-D-galactosidase which reacts with β-D-galactosidase to produce fluorescence include 4-methylumbelliferyl-β-D-galactopyranoside or analogs thereof.

In case of using β-glucuronidase as the enzyme, examples of the substrate of β-glucuronidase which reacts with β-glucuronidase to produce fluorescence include Tokyo Green™-3GluU (manufactured by Sekisui Medical Co. Ltd.).

(B-2) In Case the Label is a Fluorescent Substance

In case the label is a fluorescent substance, for example, the measurement can be carried out by measuring the intensity of fluorescence originated from the fluorescent substance in the formed inununocomplexes using a fluorescence intensity meter or the like. The fluorescent substance is not particularly limited as long as it is a fluorescent substance that enables the measurement of the present invention, and examples include fluorescein isothiocyanate (FITC) and rhodamine B-isothiocyanate (RITC), quantum dot (Science, 281, 2016-2018, 1998), phycobiliproteins such as phycoerythrin, green fluorescent protein (GFP), red fluorescent protein (RFP), yellow fluorescent protein (YFP), and blue fluorescent protein (BFP).

(C) Measurement of Absorbance

Absorbance can be measured by methods such as the following.

(C-1) In Case the Label is an Enzyme

In case the label is an enzyme, for example, the measurement can be carried out by allowing a substrate that forms a dye upon reacting with that enzyme to act on the labeled antibody or a fragment thereof, and measuring the absorbance of the formed dye using a spectrophotometer, a multi-well plate reader, or the like. The enzyme is not particularly limited as long as it can react with the substrate of the enzyme to form a dye, and examples include peroxidase.

In case using peroxidase as the enzyme, examples of the substrate of peroxidase which reacts with peroxidase to form a dye include a combination of hydrogen peroxide and an oxidative coloring type chromogen. Examples of the oxidative coloring type chromogen include leuco-type chromogens and oxidative coupling coloring chromogens.

The leuco-type chromogen is a substance that is converted into a dye by itself in the presence of hydrogen peroxide and a peroxidative substance such as peroxidase. Specific examples include tetramethylbenzidine, o-phenylenediamine, 10-N-carboxymethylcarbamoyl-3,7-bis(dimethylamino)-10 OH-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 4,4'-bis (dimethylamino)diphenylamine, and bis[3-bis(4-chlorophenyl)methyl-4-dimethylaminophenyl]amine (BCMA).

The oxidative coupling-coloring chromogen is a substance that forms a dye by oxidative coupling of two compounds in the presence of hydrogen peroxide and a peroxidative substance such as peroxidase. Examples of the combination of two compounds include a combination of a coupler and an aniline compound (Trinder reagent), and a combination of a coupler and a phenol compound. Examples of the coupler include 4-aminoantipyrine (4-AA) and 3-methyl-2-benzothiazolinonehydrazine. Examples of the aniline compound include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-bis(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS). Examples of the phenol compound include phenol, 4-chlorophenol, 3-methylphenol, and 3-hydroxy-2,4,6-triiodobenzoic acid (HTIB).

Determination of the FGF-23 concentration in a sample based on the values from measurements of the immunocomplexes formed on the magnetic particles can be carried out, for example, by the following methods.

The above-mentioned steps (1) to (3) are carried out using known concentrations of FGF-23 to give a calibration curve showing the relationship between the FGF-23 concentrations and the measured values (amount of information derived from the label), and then measurements are carried out using the samples to be measured, and the concentration of FGF-23 in the sample to be measured is determined by comparing the obtained measured values with the calibration curve prepared in advance.

(Sample)

The sample in the present invention is not particularly limited as long as it is a sample that enables the measurement of FGF-23 of the present invention. Examples include whole blood, blood plasma, serum, spinal fluid, saliva, amniotic fluid, urine, sweat, and pancreatic juice; and blood plasma and serum are preferred.

(Aqueous Medium)

The aqueous medium used in the present invention is not particularly limited so long as it is an aqueous medium which enables measurement of the FGF-23 of the present invention, and examples include deionized water, distilled water, and buffer; and a buffer is preferred. A buffer agent used for preparing a buffer is not particularly limited as long as it has buttering ability. Examples of the buffer include a buffer with pH 1 to 11, such as lactate buffer, citrate buffer, acetate buffer, succinate buffer, phthalate buffer, phosphate buffer, triethanolamine buffer, diethanolamine buffer, lysine buffer, barbiturate buffer, imidazole butter, malate butter, oxalate buffer, glycine buffer, borate buffer, carbonate buffer, glycine buffer, or Good's buffer.

Examples of the Good's buffer include 2-morpholinoethanesulfonic acid (MES) buffer, bis(2-hydroxyethyl)iminotris(hydroxymethyl)methane (Bis-Tris) buffer, tris(hydroxymethyl)aminomethane (Tris) buffer, N-(2-acetoamido)imino diacetic acid (ADA) buffer, piperazine-N,N'-bis(2-ethanesulfonic acid) (PIPES) buffer, 2-[N-(2-acetamido)amino] ethanesulfonic acid (ACES) buffer, 3-morpholino-2-hydroxypropanesulfonic acid (MOPSO) buffer, 2-[N,N-bis(2-hydroxyethyl)amino]ethanesulfonic acid (BES) buffer, 3-morpholinopropanesulfonic acid (MOPS) buffer, 2-{N-[tris(hydroxymethyl)methyl]amino}ethanesulfonic acid (TES) buffer, N-(2-hydroxyethyl)-N'-(2-sulfoethyl)piperazine (HEPES) buffer, 3-[N,N-bis(2-hydroxyethyl)amino]-2-hydroxypropanesulfonic acid (DIPSO) buffer, 2-hydroxy-3-{[N-tris(hydroxymethyl)methyl]amino}propanesulfonic acid (TAPSO) buffer, piperazine-N,N'-bis(2-hydroxypropane-3-sulfonic acid) (POPSO) buffer, N-(2-hydroxyethyl)-N'-(2-hydroxy-3-sulfopropyl)piperazine (HEPPSO) buffer, N-(2-hydroxyethyl)-N'-(3-sulfopropyl)piperazine (EPPS) buffer, [N-tris(hydroxymethyl)methylglycine] (tricine) buffer, [N,N-bis(2-hydroxyethyl)glycine] (bicine) buffer, 3-[N-tris(hydroxymethyl)methyl]aminopropanesulfonic acid (TAPS) buffer, 2-(N-cyclohexylamino)ethanesulfonic acid (CHES) buffer, 3-(N-cyclohexylamino)-2-hydroxypropanesulfonic acid (CAPSO) buffer, and 3-(N-cyclohexylamino)propanesulfonic acid (CAPS) buffer.

(Magnetic Particle)

The magnetic particle of the present invention is not particularly limited as long as it is a magnetic particle that enables measurement of FGF-23 of the present invention, and examples include ferrite-coated latex and ferrite-coated polymer particles. Furthermore, to facilitate antibody binding, magnetic particle to which avidin, NeutrAvidin, or streptavidin, which have the property of binding to biotin, has been fixed on the surface can also be used. The particle diameter of the magnetic particle is not particularly limited, and is for example 1 μm to 6 μm, and preferably 1 μm to 3 μm. Commercially available magnetic particle can be used for the magnetic particle in the present invention. Examples of the commercially available magnetic particles include Dynabeads M-280 Streptavidin (manufactured by Dynal Co.), Dynabeads M-280 Tosylactivated (manufactured by Dynal Co.), Dynabeads MyOne Streptavidin T1 (manufactured by Dynal Co.), Dynabeads MyOne Tosylactivated (manufactured by Dynal Co.), Estapor (manufactured by Merck & Co.), Sera-Mag Magnetic Streptavidin Particles (manufactured by Thermo Scientific), and MAGNOTEX-SA (manufactured by JSR Co).

(Antibody)

An antibody which binds to FGF-23 of the present invention (the first antibody and the second antibody) is not particularly limited as long as it is an antibody that enables measurement of FGF-23 of the present invention, and while both polyclonal antibody and monoclonal antibody can be used, monoclonal antibody is preferred. Furthermore, in the present invention, not only full-length antibody but also fragment of the antibody can be used. Examples of the fragment of the antibody include fragment with the Fe portions removed, such as Fab obtained by papain treatment of the antibody, F(ab')$_2$ obtained by pepsin treatment of the antibody, and Fab' obtained by pepsin treatment and reduction treatment of the antibody. In case magnetic particle to which avidin. NeutrAvidin, or streptavidin has been fixed on the surface is used as a magnetic particle, a biotinylated first antibody in which biotin is bound to the first antibody can be used.

In the first antibody and second antibody, which bind to FGF-23, used in the present invention, the site of FGF-23 where the first antibody binds and the site of FGF-23 where the second antibody binds can be the same or different, and they are preferably different.

The antibody used in the present invention can be obtained by an ordinary antibody production method using, as the antigen, FGF-23 itself or a peptide corresponding to the epitope in FGF-23; in addition, the antibody can also be obtained as a commercially available product. Examples of the antibody which binds to FGF-23 include monoclonal antibodies produced by hybridomas deposited as FERM BP-7838, FERM BP-7839, FERM BP-7840, and FERM BP-8268.

In the method and reagent for measuring FGF-23 of the present invention, substances other than antibody, such as an aptamer which binds to FGF-23, can also be used instead of the antibody which binds to FGF-23.

(Measurement Reagent)

The reagent of the present invention for measuring FGF-23 in a sample can be used in the method of the present invention for measuring FGF-23 in a sample. A measurement reagent of the present invention comprises a magnetic particle, a first antibody or a fragment thereof which binds to FGF-23, and a second antibody or a fragment thereof which binds to FGF-23. The first antibody or a fragment thereof which binds to FGF-23 that is used can be bound to the magnetic particle.

In case the first antibody or a fragment thereof which binds to FGF-23 is bound to the magnetic particle, the measurement reagent of the present invention comprises the magnetic particle to which the first antibody or a fragment thereof which binds to FGF-23 is bound, and the second antibody or a fragment thereof which binds to FGF-23.

In case the first antibody or a fragment thereof which binds to FGF-23 is not bound to the magnetic particle, the measurement reagent of the present invention comprises magnetic particle to which one of two substances with affinity to each other is fixed, a first antibody or a fragment thereof to which the other of the two substances with affinity to each other is bound, and a second antibody or a fragment thereof which binds to FGF-23. Examples of combinations of the two substances with affinity to each other include combinations of avidins, such as avidin, streptavidin, and NeutrAvidin, with biotin. Examples of an embodiment of the measurement reagent of the present invention include measurement reagent comprising magnetic particle to which avidin has been fixed, a biotinylated first antibody or a fragment thereof in which a biotin is bound to the first antibody or a fragment thereof which binds to FGF-23, and the second antibody or a fragment thereof which binds to FGF-23.

In case the second antibody or a fragment thereof is labeled, the measurement reagent of the present invention further comprises a reagent for measuring the label which enables measurement of the labeled second antibody or a fragment thereof in the immunocomplexes comprising a first antibody or a fragment thereof, FGF-23, and the labeled second antibody or a fragment thereof. The reagent for measuring the label is not particularly limited as long as it is a reagent that enables measurement of the labeled second antibody or a fragment thereof in the formed immunocomplexes. Examples include a reagent for measuring chemiluminescence and a reagent for measuring fluorescence; and a reagent for measuring chemiluminescence is preferred.

In case the second antibody or a fragment thereof which binds to FGF-23 is not labeled, the measurement reagent of the present invention further comprises a labeled third antibody or a fragment thereof, in which a label is bound to a third antibody or a fragment thereof that binds to the second antibody or a fragment thereof, and a reagent for measuring the label which enables measurement of the labeled third antibody or a fragment thereof in the immunocomplexes comprising the first antibody or a fragment thereof, FGF-23, the second antibody or a fragment thereof, and the labeled third antibody or a fragment thereof. Examples of the third antibody or a fragment thereof that binds to the second antibody or a fragment thereof include an antibody or a fragment thereof that binds to the Fc region of the second antibody. The reagent for measuring the label that enables measurement of the labeled third antibody or a fragment thereof in the immunocomplexes is not particularly limited as long as it is a reagent that enables measurement of the labeled third antibody or a fragment thereof in the formed immunocomplexes. Examples include a reagent for measuring chemiluminescence, a reagent for measuring fluorescence, and a reagent for measuring absorbance; and a reagent for measuring chemiluminescence is preferred.

In particular, a reagent for measuring chemiluminescence is a reagent that is used in case the label is an enzyme, and examples include a reagent comprising a substrate of the enzyme that produces light upon reaction with that enzyme. Examples of the combinations of an enzyme and a substrate of the enzyme that forms light upon reaction with the enzyme include the aforementioned combinations.

In particular, a reagent for measuring fluorescence is a reagent that is used in case the label is an enzyme, and examples include a reagent comprising a substrate of the enzyme that produces fluorescence upon reaction with the enzyme. Examples of the combinations of an enzyme and a substrate of the enzyme that produces fluorescence upon reaction with the enzyme include the aforementioned combinations.

In particular, a reagent for measuring absorbance is a reagent that is used when the label is an enzyme, and examples include a reagent comprising a substrate of the enzyme that produces a dye upon reaction with the enzyme. Examples of the combinations of an enzyme and a substrate of the enzyme that produces a dye upon reaction with the enzyme include the aforementioned combinations.

Examples of magnetic particle, a first antibody or a fragment thereof which binds to FGF-23, and a second antibody or a fragment thereof which binds to FGF-23 used in the measurement reagents of the present invention include the aforementioned magnetic particle, a first antibody or a fragment thereof which binds to FGF-23, and a second antibody or a fragment thereof which binds to FGF-23, respectively. Furthermore, the measurement reagents of the present invention can comprise the aforementioned aqueous medium, a substrates of a labeling enzyme, a metal ion, a sugar, an antiseptic agent, a protein, a surfactant, a protein stabilizer, or such as necessary.

Herein below, the present invention will be specifically described with reference to the Examples, but the description is not to be construed as limiting the scope of the present invention.

Example 1

(1) Materials and Measurement Methods

<Samples for Measurement>

Solutions prepared by diluting serum obtained from a healthy individual (serum with FGF-23 concentration of 10 pg/mL; purchased from Aries Diagnostika GmbH) with a phosphate-buffered saline solution (10 mmol/L phosphate buffer containing 0.15 mol/L sodium chloride, pH7.2) containing 0.2% BSA (manufactured by Bovogen Biologicals Co.) to obtain FGF-23 concentrations of 9 pg/mL, 8 pg/mL, 7 pg/mL, 6 pg/mL, 5 pg/mL, 4 pg/mL, 3 pg/mL, 2 pg/mL, and 1 pg/mL; and a phosphate buffered saline solution containing 0.2% BSA (FGF-23 concentration of 0 pg/mL) were used as samples for measurement.

<Suspension Solution of Magnetic Particles>

Commercially available streptavidin-bound magnetic particles (Dynabeads MyOne Streptavidin T1; manufactured by Dynal Co.) were used as the magnetic particles to prepare a suspension solution of magnetic particles having the following composition:

| MES (pH 6.5) | 50 mmol/L |
|---|---|
| Streptavidin-bound magnetic particles | 0.75 mg/mL |
| BSA | 0.1% |
| Sodium chloride | 0.1 mol/L |

<Biotinylated Anti-FGF-23 Antibody and Biotinylated Anti-FGF-23 Antibody Solution>

The anti-FGF-23 monoclonal antibody 2C3B produced by the hybridoma deposited as FERM BP-7838 was used as the first antibody. This antibody and NHS-biotin were mixed and reaction was carried out at 37° C. for one hour, and the reacted mixture was subjected to a Sephadex G-25 column (manufactured by GE Health Science Japan Co.) to remove the unreacted NHS-biotin, and the biotinylated anti-FGF-23 monoclonal antibody was prepared. Using the obtained biotinylated anti-FGF-23 monoclonal antibody, a biotinylated anti-FGF-23 antibody solution having the following composition was prepared:

| MES (pH 6.5) | 50 mmol/L |
|---|---|
| anti-FGF-23 monoclonal antibody 2C3B | 5 µg/mL |
| BSA | 0.1% |
| Sodium Chloride | 0.1 mol/L |

<Alkaline Phosphatase-Labeled Anti-FGF-23 Antibody Fragment and Alkaline Phosphatase-Labeled Anti-FGF-23 Antibody Fragment Solution>

For the second antibody fragment, the anti-FGF-23 monoclonal antibody 3C1E produced by the hybridoma deposited as FERM BP-7839 was subjected to pepsin digestion, and then $F(ab')_2$ was separated by the HPLC system (manufactured by Hitachi Ltd.) using a G3000SW column (manufactured by Tosoh Co.; diameter: 21.5 mm; length: 60 cm). After reducing the obtained $F(ab')_2$ using 2-mercaptoethylamine hydrochloride (manufactured by Nacalai Tesque), Fab' were separated by the HPLC system (manufactured by Hitachi Ltd.) using a G3000SW column (manufactured by Tosoh Co.; diameter: 21.5 mm; length: 60 cm). The obtained Fab' and alkaline phosphatase were bound by the maleimide method according to the following procedure.

Using the maleimidization reagent Sulfo-HMCS (manufactured by Dojindo Laboratories), alkaline phosphatase was maleimidized, and the reaction mixture was subjected to a Sephadex G-25 column (manufactured by GE Health Science Japan Co.) to remove the unreacted Sulfo-HMCS, and the maleimidized alkaline phosphatase was obtained.

The prepared maleimidized alkaline phosphatase and Fab' were mixed, and the alkaline phosphatase-labeled Fab' antibody was obtained. The obtained alkaline phosphatase-labeled Fab' antibody was used to prepare the alkaline phosphatase-labeled anti-FGF-23 antibody fragment solution having the following composition:

| MES (pH 6.5) | 50 mmol/L |
|---|---|
| alkaline phosphatase-labeled anti-FGF-23 antibody fragment | 5 µg/mL |
| BSA | 0.1% |
| Sodium Chloride | 0.1 mol/L |

(2) Measurement of FGF-23 in the Samples

To 10 µL of the sample for measurement prepared in (1) described above, 30 µL each of the magnetic particle suspension solution, biotinylated anti-FGF-23 antibody solution, and alkaline phosphatase-labeled anti-FGF-23 antibody fragment solution prepared in (1) were added and the mixture was stirred, and reaction was carried out at 37° C. for 20 minutes. The magnetic particles were collected by magnetic force to remove the reaction solution apart from the magnetic particles, and the magnetic particles were washed five times using a washing solution [50 mmol/L MOPS buffer containing 0.1% Tween 20 (pH 7.35)]. Thereafter, 100 µL of a luminescent substrate solution containing 9-(4-chlorophenylthiophosphoryloxymethylidene)-10-methylacridan disodium salt as the major component was added and the mixture was stirred, and the level of produced luminescence (RLU) was measured. The results of the measurement are shown in FIG. 1.

A method for defining the minimum measurable concentration for the measurement system includes the method of statistical evaluation using the average values and standard deviation. Specifically, if the average value of a five-time-measurement of a sample prepared in (1) minus twice the standard deviation (−2SD) has an RLU that is higher than that of the average value of a five-time-measurement of the 0 pg/mL sample plus twice the standard deviation (+2SD), that sample can be defined as having a detectable concentration.

When the sample having an FGF-23 concentration of 0 pg/mL was measured, the average luminescence level plus 2SD was 173 RLU (dotted line of FIG. 1). On the other hand, when a sample having an FGF-23 concentration of 1 pg/mL was measured, the average luminescence level minus 2SD was 186 RLU, which is a higher value than the average luminescence level plus 2SD obtained when the 0 pg/mL sample was measured. Thus, this confirmed that 1 pg/mL of FGF-23 was measurable. Accordingly, in this measurement method, the minimum concentration of FGF-23 that can be detected can be defined as being 1 pg/mL. Furthermore, as shown in FIG. 1, at an FGF-23 concentration of 1 pg/mL or higher, a concentration-dependent increase in the luminescence level was observed.

Example 2

(1) Materials and Measurement Methods

<Samples for Measurement>

Solutions prepared by diluting FGF-23 produced according to the method described in WO02003/057733 with a phosphate-buffered saline solution (10 mmol/L phosphate buffer containing 0.15 mol/L sodium chloride, pH7.2) containing 0.2% BSA (manufactured by Bovogen Biologicals Co.) to obtain FGF-23 concentrations of 10,000 pg/mL, 3.000 pg/mL, 1,000 pg/mL, 300 pg/mL, 100 pg/mL, 50 pg/mL, 10 pg/mL, and 5 pg/mL; and a phosphate buffered saline solution containing 0.2% BSA (FGF-23 concentration of 0 pg/mL) were used for the samples for measurement.

(2) Measurement of FGF-23 in the Samples

Measurements were carried out by the same method as in Example 1, except that the samples for measurement of (1) above were used. The results are shown in FIG. 2.

Figure 2:
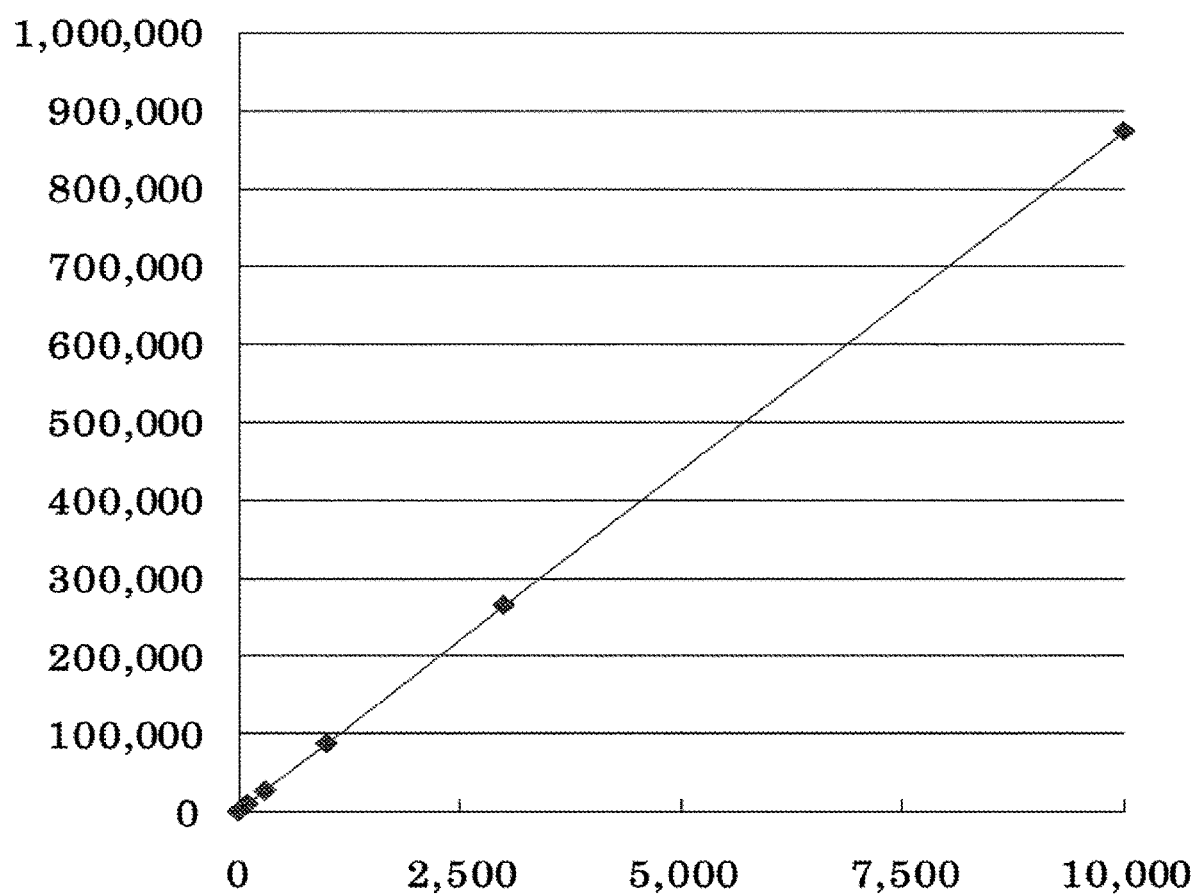
FIG. 2 shows a graph indicating the measurement range of the method for measuring FGF-23 of Example 2, and shows the relationships between the FGF-23 concentrations in the samples and the luminescence levels. The horizontal axis shows the FGF-23 concentration (pg/mL), and the vertical axis shows the luminescence level (RLU).

As is apparent from FIG. 2, in the concentration range of 5 pg/mL to 10,000 pg/mL, the luminescence level was found to increase dependent on FGF-23 concentration and in linear manners. Therefore, it proved that FGF-23 concentrations could be measured in the range of 5 pg/mL to 10,000 pg/mL using the measurement method of the present invention.

Example 3

Artificial dialysis refers to removing waste products, maintaining electrolytes, and maintaining water content in the blood by external means, and to avoid coagulation of the blood circulating outside the body, an anticoagulant (heparin) is used. Therefore, in a dialysis patient specimen, deposition of fibrin is often observed after serum separation. When deposited fibrin is present in the serum, the FGF-23 measurement system may be affected and accurate results may not be obtained.

Simultaneous repeatability test, spike-recovery test, and dilution linearity test are often carried out as methods for determining whether or not accurate measurements are being obtained. Accordingly, the following simultaneous repeatability test, spike-recovery test, and dilution linearity test were carried out for the measurement method of Example 1 using sera derived from dialysis patients (purchased from Discovery Life Sciences Inc).

(1) Simultaneous Repeatability Test

Simultaneous repeatability test is a method for determining the accuracy of a measurement method by carrying out multiple, successive measurements using the same sample (serum, plasma, etc.) to evaluate the variation in the measured values.

Using three types of dialysis patient-derived sera, the FGF-23 concentration in each serum was measured ten times according to the method described in Example 1. The FGF-23 concentrations, their averages, and the coefficients of variation (CV %) obtained by the measurements are shown in Table 1. The coefficient of variation for each serum was 1.2% to 3.1% and was favorable. Therefore, it proved that FGF-23 in sera derived from dialysis patients can be measured with good reproducibility using the measurement method of the present invention.

TABLE 1

| | FGF-23 CONCENTRATION (pg/mL) | | |
|---|---|---|---|
| | PATIENT A | PATIENT B | PATIENT C |
| | 370.4 | 173.7 | 1904.6 |
| | 366.3 | 165.6 | 1895.4 |
| | 374.0 | 170.6 | 1868.0 |
| | 367.1 | 172.0 | 1906.8 |
| | 372.5 | 173.5 | 1946.6 |
| | 346.9 | 164.8 | 1914.0 |
| | 361.7 | 170.9 | 1914.3 |
| | 345.8 | 166.4 | 1899.4 |
| | 347.4 | 172.2 | 1875.8 |
| | 351.4 | 163.8 | 1915.3 |
| AVERAGE | 360.4 | 169.3 | 1904.0 |
| CV % | 3.1 | 2.2 | 1.2 |

Spike-recovery test is a method for determining the accuracy of a measurement method by measuring samples (serum, plasma, etc.) with known concentrations of an antigen (FGF-23) added and evaluating whether the measurements match with the actual added amounts.

Three types of sera originated from dialysis patient to which FGF-23 prepared by the method described in WO2003/057733 was added at various concentrations were used as the measurement samples and measured by the method described in Example 1 to carry out the spike-recovery tests. The spike-recovery rates are shown in Table 2. The spike-recovery rate for each serum was 96.7% to 101.6% and was favorable. Therefore, it proved that FGF-23 in sera derived from dialysis patients can be accurately measured using the measurement method of the present invention.

(3) Dilution Linearity Test

TABLE 2

| | FGF-23 IN SERUM pg/mL | ADDED FGF-23 pg/mL | ADDITION-RECOVERY RATE % |
|---|---|---|---|
| PATIENT SERUM 1 | 151.2 | 27.8 | 98.1 |
| | | 87.0 | 97.7 |
| | | 260.8 | 96.7 |
| PATIENT SERUM 2 | 1583.7 | 260.8 | 99.6 |
| | | 877.4 | 97.3 |
| | | 2204.4 | 100.0 |
| PATIENT SERUM 3 | 2178.2 | 260.8 | 101.6 |
| | | 877.4 | 98.0 |
| | | 2204.4 | 98.3 |

Dilution linearity test is a method for determining the accuracy of a measurement method by carrying out a stepwise dilution of a sample (serum, plasma, etc.) using an appropriate diluent, and evaluating whether or not the measured values decrease linearly in accordance with the degree of dilution.

Two types of dialysis patient-derived sera (patient serum D and patient serum E) subjected to ten-step dilution using a phosphate buffered saline solution containing 0.2% BSA (manufactured by Bovogen Biologicals Co.) and a phosphate buffered saline solution containing 0.2% BSA (FGF-23 concentration of 0 pg/mL) were used as the samples for measurement and measured by the method described in Example 1 to carry out the dilution linearity test.

Figure 3:
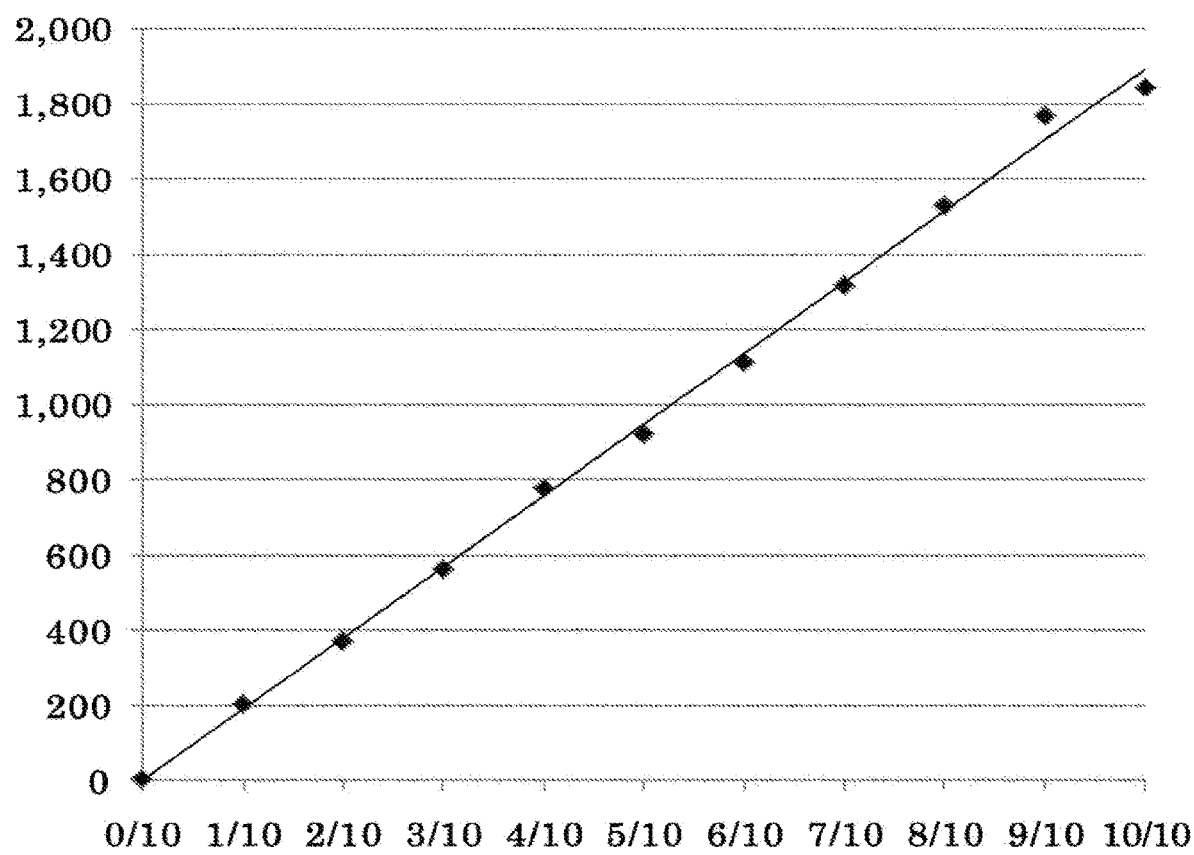
FIG. 3 shows a graph indicating the dilution linearity in the measurement_method of Example 3 which uses a dialysis patient-derived serum (patient serum D), and shows the relationship between the dilution rate and FGF-23 concentration. The horizontal axis shows the dilution rate of the serum and the vertical axis shows the determined FGF-23 concentrations (pg/mL).
Figure 4:
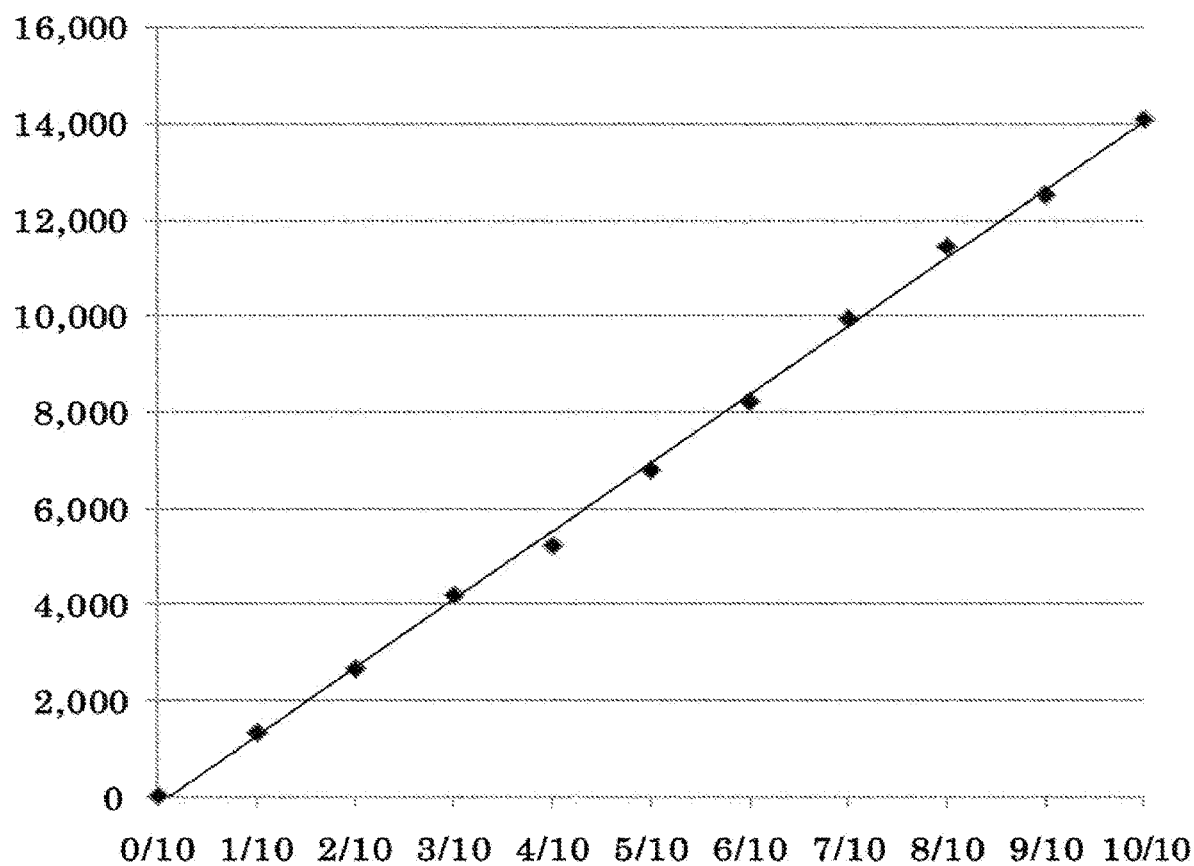
FIG. 4 shows a graph indicating the dilution linearity in the measurement_method of Example 3 which uses a dialysis patient-derived serum (patient serum E), and shows the relationship between the dilution rate and FGF-23 concentration. The horizontal axis shows the dilution rate of the serum and the vertical axis shows the determined FGF-23 concentrations (pg/mL).

The results of plotting the dilution rates (x-axis) and the FGF-23 concentrations determined by the measurements (y-axis) are shown in FIGS. 3 and 4. Since a good linearity was obtained from both dialysis patient-derived sera, it proved that FGF-23 in the sera derived from dialysis patients can be accurately measured using the measurement method of the present invention.

Comparative Example 1

(1) Materials and Measurement Methods
<Samples for Measurement>

Solutions prepared by diluting a serum obtained from a healthy individual (serum with FGF-23 concentration of 20 pg/mL; purchased from Aries) with a phosphate-buffered saline solution (10 mmol/L phosphate buffer containing 0.15 mol/L sodium chloride, pH7.2) containing 0.2% BSA (manufactured by Bovogen Biologicals Co.) to obtain FGF-23 concentrations of 16 pg/mL, 14 pg/mL, 12 pg/mL, 10 pg/mL, 8 pg/mL, 6 pg/mL, 4 pg/mL, and 2 pg/mL; and a phosphate buffered saline solution containing 0.2% BSA (FGF-23 concentration of 0 pg/mL) were used for the samples for measurement.

(2) Measurement of FGF-23 in the Samples

The reagent for measuring FGF-23 for a plate method (manufactured by Kainos) was used for the measurement kit, the samples for measurement prepared in (1) were used as the samples, and measurements were taken five times by a similar method as in Example 1. The results are shown in FIG. 5.

Figure 5:
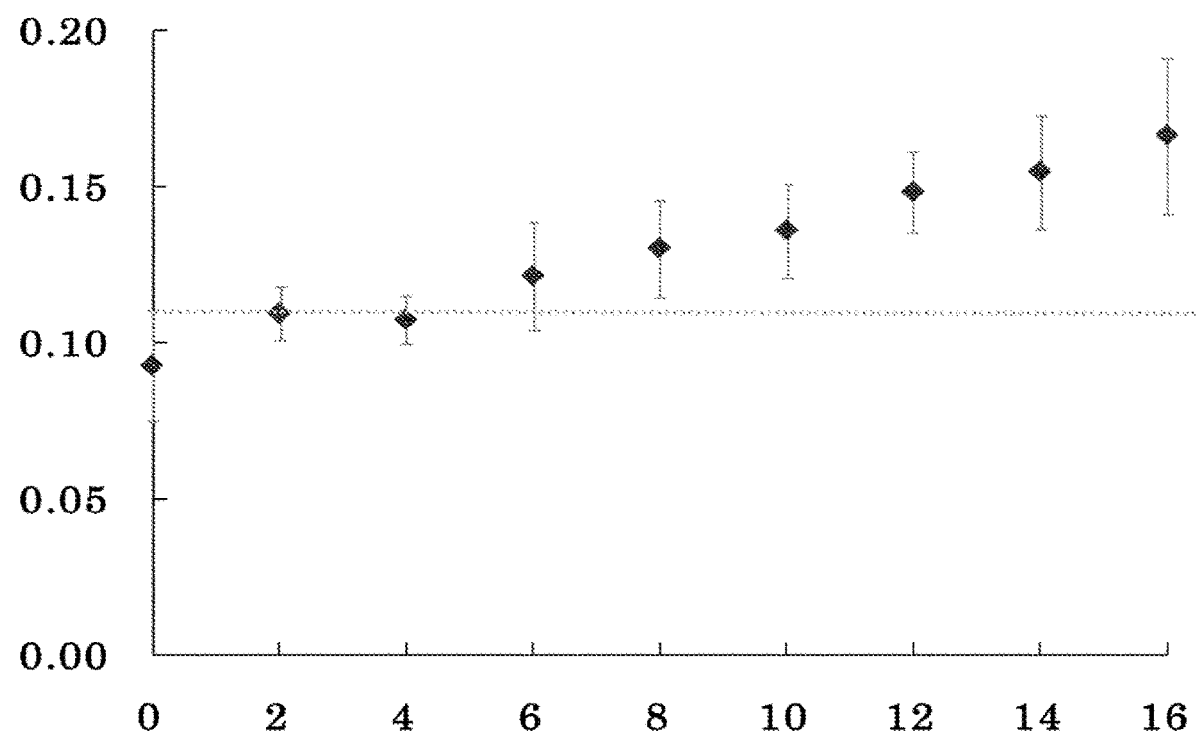
FIG. 5 shows a graph indicating the minimum measurable concentrations using the method for measuring FGF-23 of Comparative Example 1 which uses a plate, and shows the relationship between the FGF-23 concentrations in the samples and the absorbances. The horizontal axis shows the FGF-23 concentration (pg/mL), and the vertical axis shows the absorbance (Abs). The mark "I" indicates the ranges of the average values±2SD. Furthermore, the dotted line shows the absorbance of blank±2SD.

When the sample having an FGF-23 concentration of 0 pg/mL was measured, the average absorbance plus 2SD was 0.111 (dotted line of FIG. 5). When a sample having an FGF-23 concentration of 6 pg/mL was measured, the average absorbance minus 2SD was 0.104, which is a lower value than the average absorbance plus 2SD obtained when the 0 pg/mL sample was measured. Thus, it proved that an FGF-23 having a concentration of 6 pg/mL cannot be measured. On the other hand, when a sample having an FGF-23 having a concentration of 8 pg/mL was measured, the average absorbance minus 2SD was 0.115, which is a higher value than the average absorbance plus 2SD obtained when the 0 pg/mL sample was measured. Thus, it proved that FGF-23 at 8 pg/mL is measurable. Accordingly, in this measurement method, the minimum concentration of FGF-23 that can be detected can be defined as being 8 pg/mL.

Comparative Example 2

Figure 6:
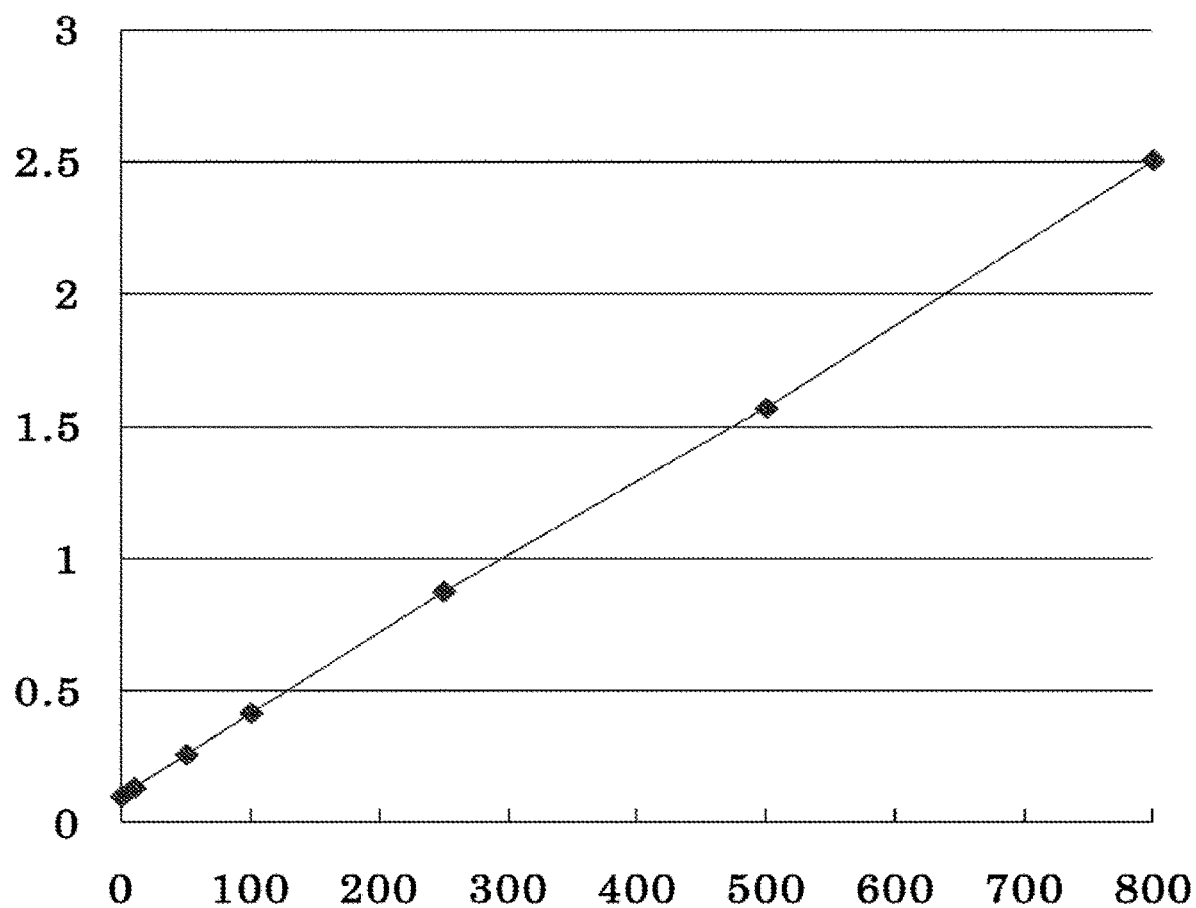
FIG. 6 shows a graph indicating the measurement range of the method for measuring FGF-23 of Comparative Example 2 which uses a plate, and shows the relationship between the FGF-23 concentrations in the samples and the absorbances. The horizontal axis shows the FGF-23 concentration (pg/mL), and the vertical axis shows the absorbance (Abs).

Using the reagent for measuring FGF-23 (manufactured by Kainos; plate method), the standard solutions attached to the reagent (FGF-23 concentrations of 0 pg/mL, 10 pg/mL, 50 pg/mL, 100 pg/mL, 250 pg/mL, 500 pg/mL, and 800 pg/mL) was measured, and their absorbances are shown in FIG. 6. The absorbance increased dependent on an FGF-23 concentration from 10 pg/mL to 800 pg/mL. The upper limit of the measurement range of the FGF-23 measurement reagent is defined as being 800 pg/mL, so that higher concentrations of FGF-23 cannot be quantified.

On the other hand, as shown in Example 2, in the method of the present invention, measurements are possible from 5 pg/mL to 10,000 pg/mL; therefore, it proved that the measurement method of the present invention was a method with higher sensitivity and wider measurement range as compared to the plate method.

INDUSTRIAL APPLICABILITY

The present invention provides a method and a reagent for measuring FGF-23 in a sample, which have a high sensitivity and a wide measurement range, and are effective for diagnosis of diseases such as hypophosphatemic rickets, neoplastic osteomalacia, and renal failure.

The invention claimed is:

1. A method for measuring fibroblast growth factor-23 (FGF-23) in a sample, wherein the method comprises the steps of:
    (1) reacting, in an aqueous medium, FGF-23 in a sample with a magnetic particle bonded with a first antibody or a fragment thereof which binds to FGF-23, and a second antibody or a fragment thereof which binds to FGF-23, to form on the magnetic particle an immunocomplex comprising the first antibody or a fragment thereof which binds to FGF-23, FGF-23, and the second antibody or a fragment thereof which binds to FGF-23,
    wherein the sample comprises FGF-23 in a concentration ranging from 5 pg/mL to 10,000 pg/mL;
    (2) collecting the magnetic particle in the reaction mixture after step (1) by magnetic force, and separating the magnetic particle collected by magnetic force from the other components; and
    (3) measuring the immunocomplex on the magnetic particle separated in step (2).

2. The method of claim 1, wherein the second antibody is a labeled antibody.

3. The method of claim 2, wherein the labeled antibody is an alkaline phosphatase-labeled antibody.

4. The method of claim 1, wherein measurement of the immunocomplex on the magnetic particle in step (3) is carried out by measurement of chemiluminescence.

5. The method of claim 1, wherein the sample is serum or plasma.

6. The method of claim 1, wherein the sample comprises FGF-23 in a concentration ranging from 5 pg/mL to 3,000 pg/mL.

7. The method of claim 1, wherein the sample comprises FGF-23 in a concentration ranging from 5 pg/mL to 1,000 pg/mL.

* * * * *